(12) United States Patent
Kanaya et al.

(10) Patent No.: US 10,040,053 B2
(45) Date of Patent: Aug. 7, 2018

(54) PRODUCTION METHOD FOR POROUS CELLULOSE BEADS, AND ADSORBENT EMPLOYING SAME

(71) Applicant: KANEKA CORPORATION, Osaka-shi (JP)

(72) Inventors: Kento Kanaya, Takasago (JP); Yoshikazu Kawai, Takasago (JP); Takahiro Okubo, Takasago (JP); Ken-ichiro Morio, Osaka (JP)

(73) Assignee: KANEKA CORPORATION, Osaka-shi (JP)

( * ) Notice: Subject to any disclaimer, the term of this patent is extended or adjusted under 35 U.S.C. 154(b) by 144 days.

(21) Appl. No.: 15/029,293

(22) PCT Filed: Oct. 14, 2014

(86) PCT No.: PCT/JP2014/077360
§ 371 (c)(1),
(2) Date: Apr. 14, 2016

(87) PCT Pub. No.: WO2015/056679
PCT Pub. Date: Apr. 23, 2015

(65) Prior Publication Data
US 2016/0251394 A1 Sep. 1, 2016

(30) Foreign Application Priority Data
Oct. 15, 2013 (JP) .................................. 2013-215119

(51) Int. Cl.
*B01J 20/24* (2006.01)
*B01J 20/285* (2006.01)
(Continued)

(52) U.S. Cl.
CPC .......... *B01J 20/3274* (2013.01); *B01D 15/00* (2013.01); *B01J 20/24* (2013.01); *B01J 20/267* (2013.01);
(Continued)

(58) Field of Classification Search
None
See application file for complete search history.

(56) References Cited

U.S. PATENT DOCUMENTS

2010/0184957 A1* 7/2010 Kawai .................... B01D 15/00
530/387.1
2013/0331563 A1 12/2013 Kawai et al.

FOREIGN PATENT DOCUMENTS

CA   2 828 369 A1   9/2012
JP   2001-139938 A   5/2001
(Continued)

OTHER PUBLICATIONS

Sigma et al. ("Cellulase from Aspergillus niger", accessed online Oct. 27, 2017, pp. 1-4). (Year: 2017).*
(Continued)

*Primary Examiner* — Clare M Perrin
(74) *Attorney, Agent, or Firm* — Oblon, McClelland, Maier & Neustadt, L.L.P.

(57) ABSTRACT

The objective of the present invention is to provide to a method for easily producing high-performance porous cellulose beads having high mechanical strength. Also, the objective of the present invention is to provide an adsorbent produced from the high-performance porous cellulose beads. According to the present invention, high-performance porous cellulose beads can be easily produced from porous cellulose beads, and an adsorbent having high strength and high adsorption amount can be easily produced from the high-performance porous cellulose beads.

7 Claims, 7 Drawing Sheets

(51) Int. Cl.
| | |
|---|---|
| B01D 15/00 | (2006.01) |
| B01J 20/32 | (2006.01) |
| C02F 1/28 | (2006.01) |
| C12P 19/14 | (2006.01) |
| B01J 20/26 | (2006.01) |
| B01J 20/30 | (2006.01) |
| B01J 20/28 | (2006.01) |
| C08J 9/00 | (2006.01) |
| B01J 20/00 | (2006.01) |
| B01J 39/00 | (2006.01) |
| C02F 1/42 | (2006.01) |
| C02F 1/52 | (2006.01) |
| B01D 21/01 | (2006.01) |
| C07K 1/22 | (2006.01) |
| C08J 9/26 | (2006.01) |
| G01N 30/52 | (2006.01) |
| B01J 20/286 | (2006.01) |

(52) U.S. Cl.
CPC ....... *B01J 20/285* (2013.01); *B01J 20/28016* (2013.01); *B01J 20/3085* (2013.01); *B01J 20/3212* (2013.01); *C02F 1/286* (2013.01); *C08J 9/00* (2013.01); *C12P 19/14* (2013.01); *B01J 20/286* (2013.01); *B01J 2220/54* (2013.01); *B01J 2220/82* (2013.01); *C07K 1/22* (2013.01); *C08J 9/26* (2013.01); *C08J 2201/026* (2013.01); *C08J 2201/046* (2013.01); *C08J 2301/02* (2013.01); *G01N 2030/525* (2013.01)

(56) References Cited

FOREIGN PATENT DOCUMENTS

| | | | |
|---|---|---|---|
| JP | 2009-247981 A | | 10/2009 |
| JP | 2009247981 A | * | 10/2009 |
| JP | 2011-252929 A | | 12/2011 |
| WO | 2008/146906 A1 | | 12/2008 |

OTHER PUBLICATIONS

Wood et al. (Methods in Enzymology: Chapter 9: "Methods for Measuring Cellulase Activities", 1988, vol. 160, pp. 87-112).*
Machine translation of JP # 2009247981, pp. 1-13.*
Roy et al. (Bioseparation, 1999, 8, pp. 317-326).*
Buschle-Diller et al. ("Effect of cellulose on the pore structure of bead cellulose", Cellulose, 1995, 2, 179-203.*
Chen, et al. ("Physcial Characteristics of Porous Cellulose Beads as Supporting Material for Immobilized Enzymes", Biotechnology and Bioengineering, 18, 1507-1516.*
Yang et al. (Journal of Applied Polymer Science, 2011, 119, 1204-1210).*
Extended European Search Report dated May 19, 2017 in Patent Application No. 14953421.7.
Ipsita Roy, et al. "Comparison of batch, packed bed and expanded bad purification of *A. niger* cellulase using cellulose beads," Bioseparation. Kluwer Academic Publishers. vol. 8, No. 6, XP002658820, 1999, pp. 317-326.
Gisela Buschie-Diller, et al. "Effect of cellulase on the pore structure of bead cellulose," Cellulose, vol. 2, No. 3, XP55371725A, 1995, pp. 179-203.
Alon Y. Hershko, et al., "Removal of Pathogenic Autoantibodies by Immunoadsorption," Annals of the New York Academy of Sciences, vol. 1051, 2005, pp. 635-646.
Alexander Staudt, et al., "Immunoadsorption in dilated cardiomyopathy: 6-month results from a randomized study," American Heart Journal, vol. 152, No. 4, Oct. 2006, (6 pages).
International Search Report dated Jan. 27, 2015 in PCT/JP2014/077360 filed Oct. 14, 2014.

* cited by examiner

[Fig. 1]
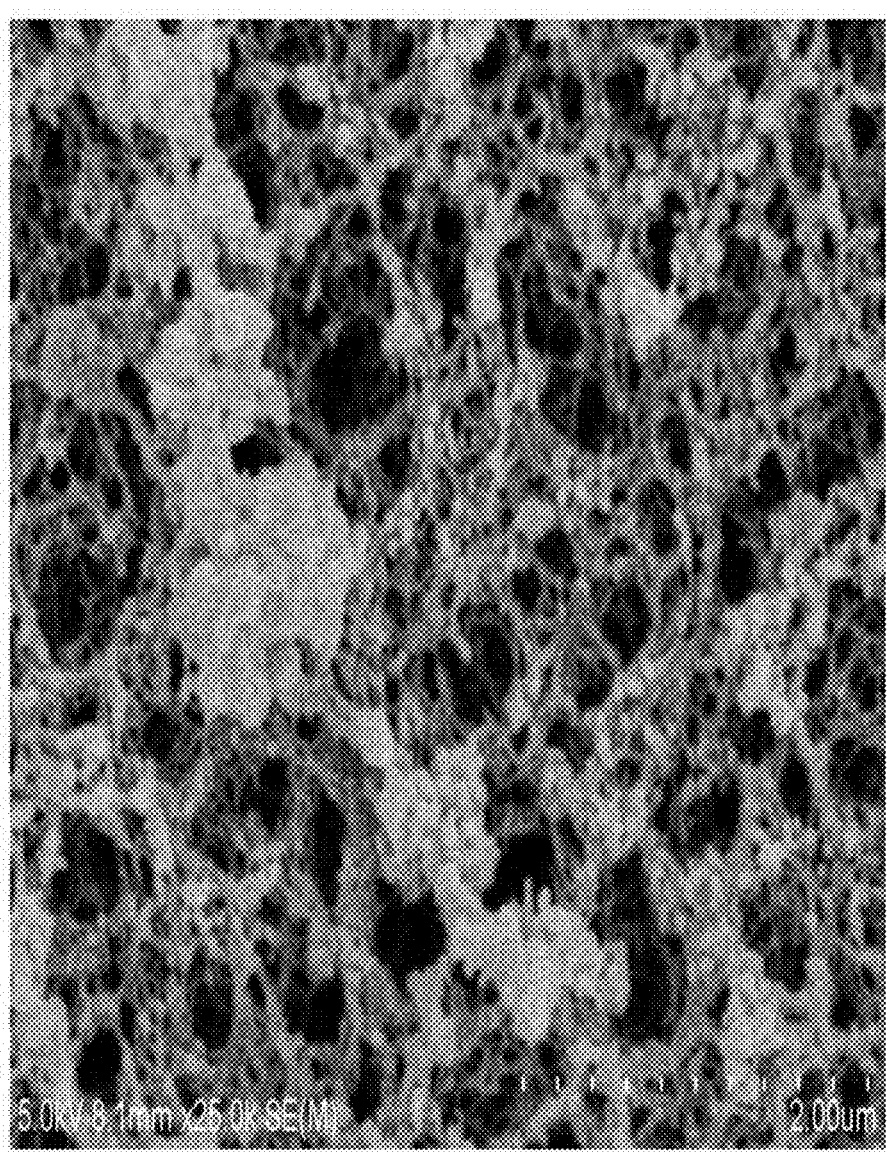

[Fig. 2]
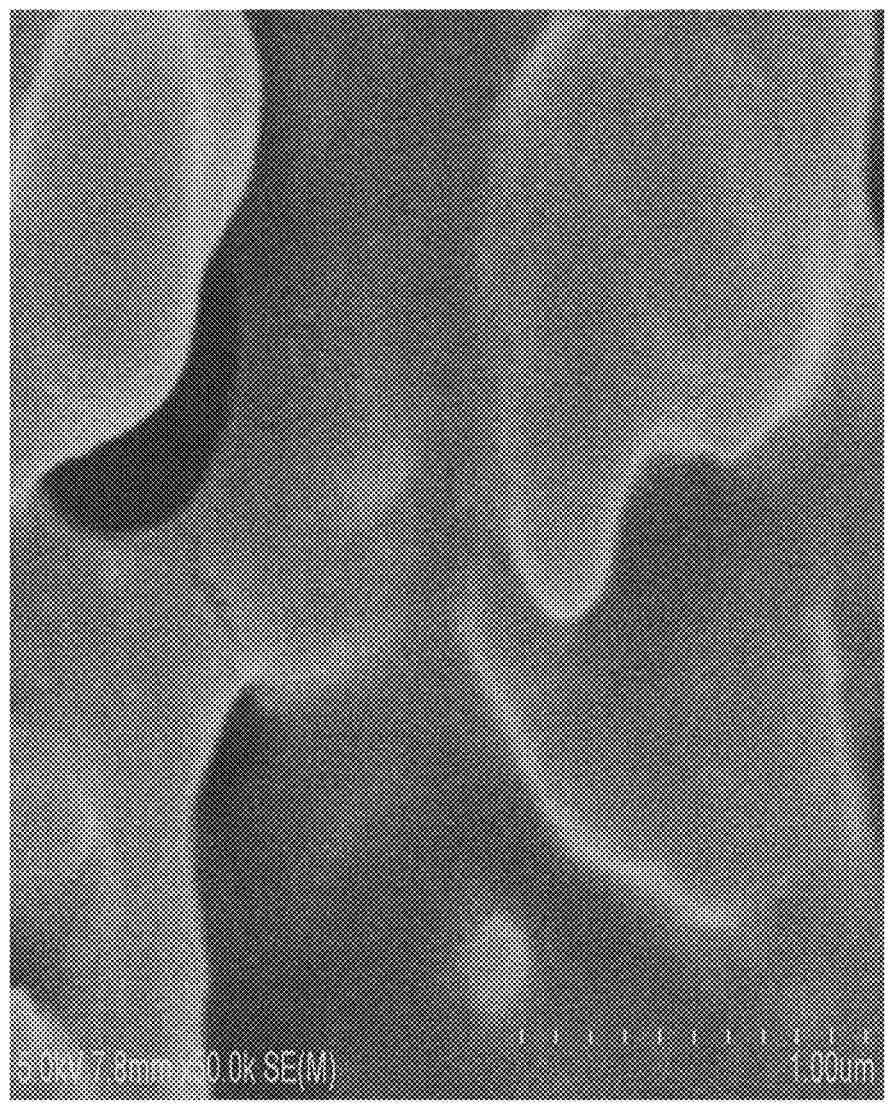

[Fig. 3]
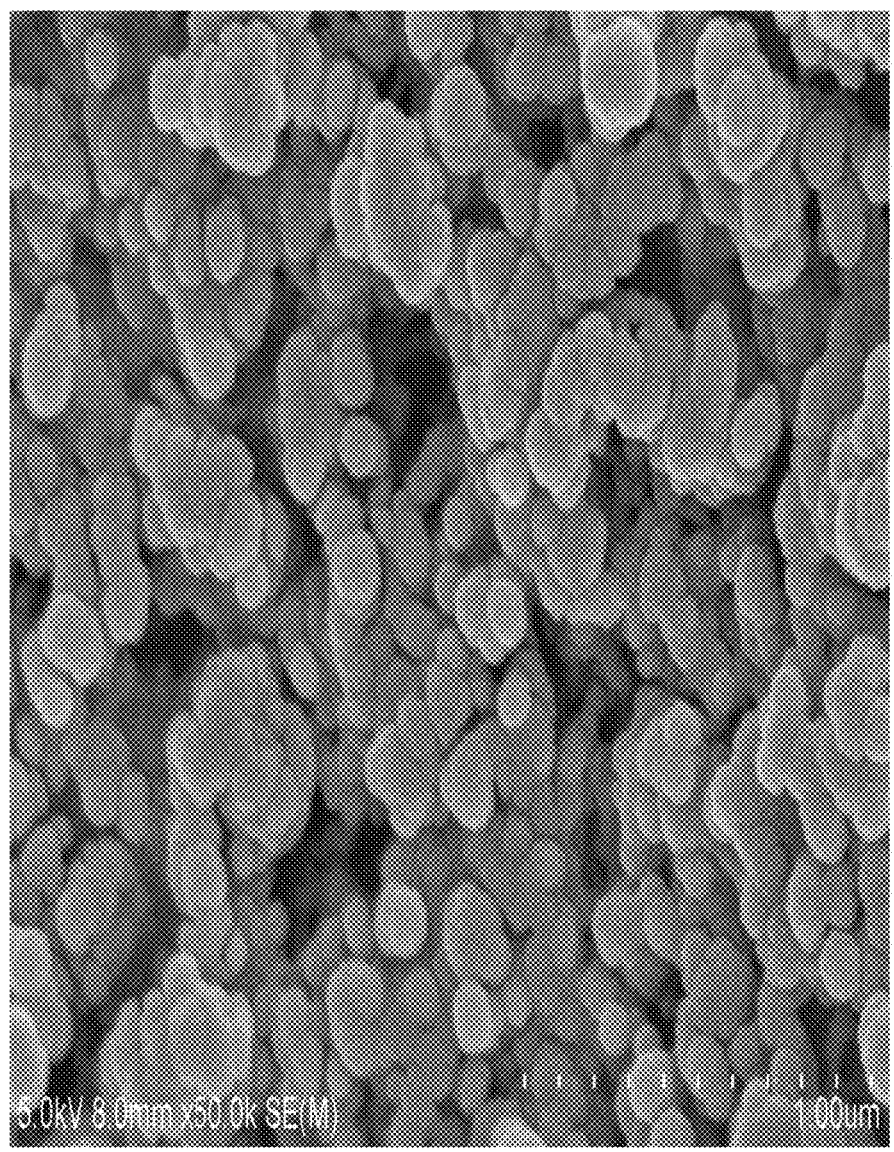

[Fig. 4]
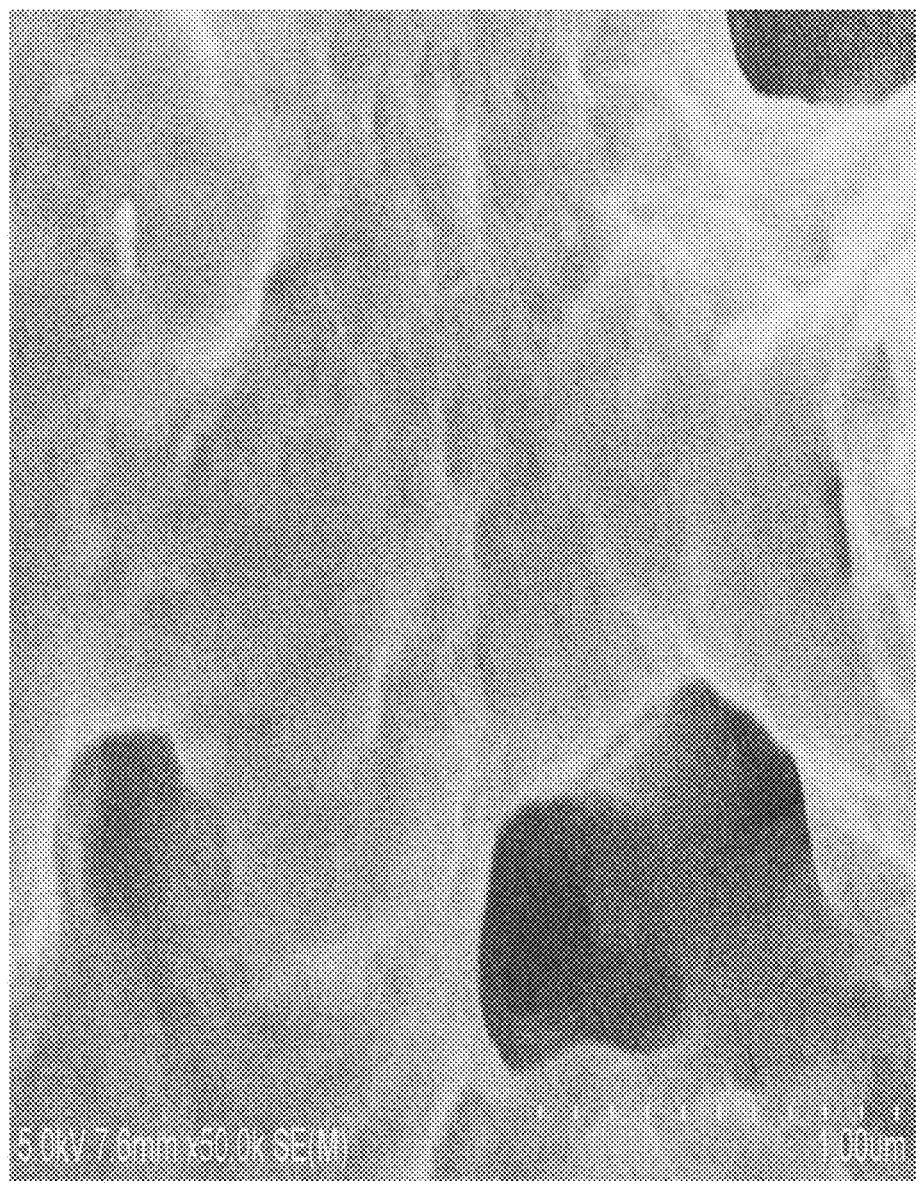

[Fig. 5]
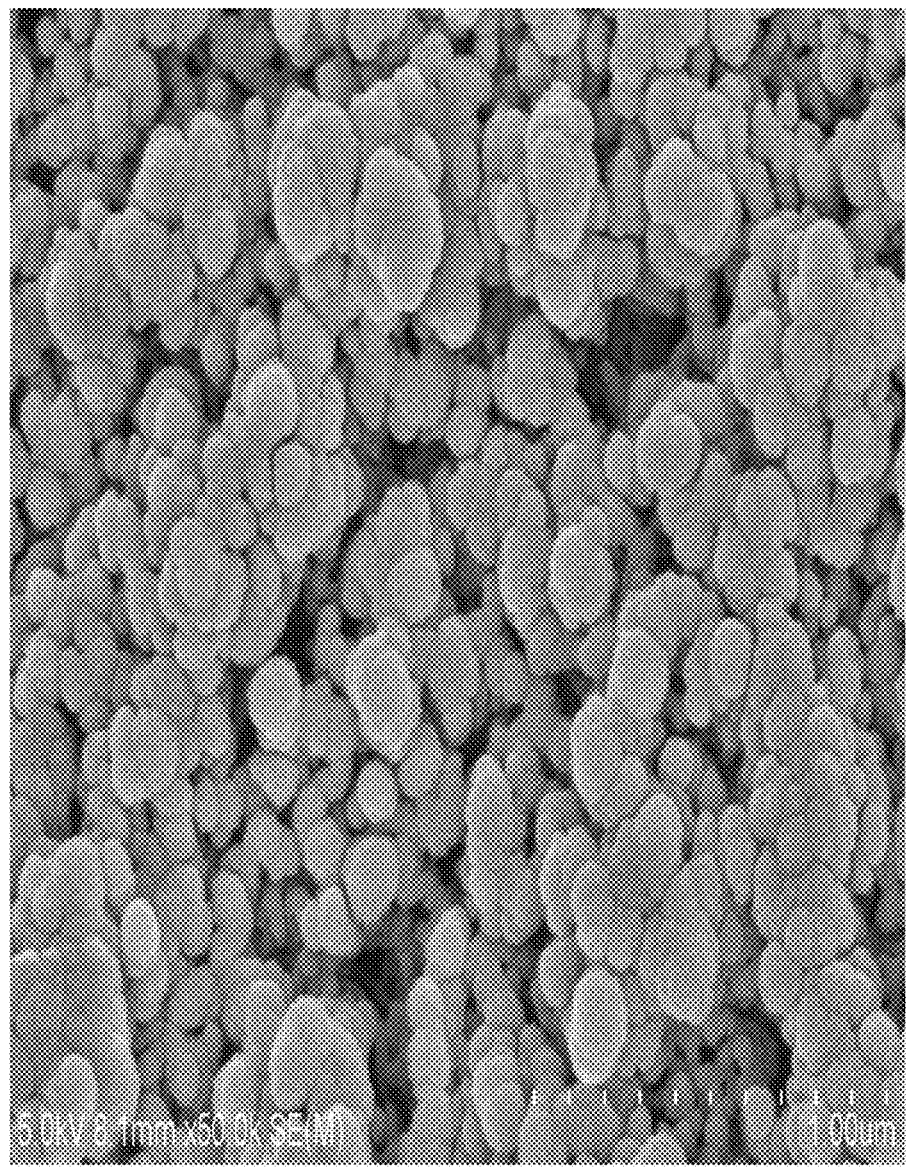

[Fig. 6]
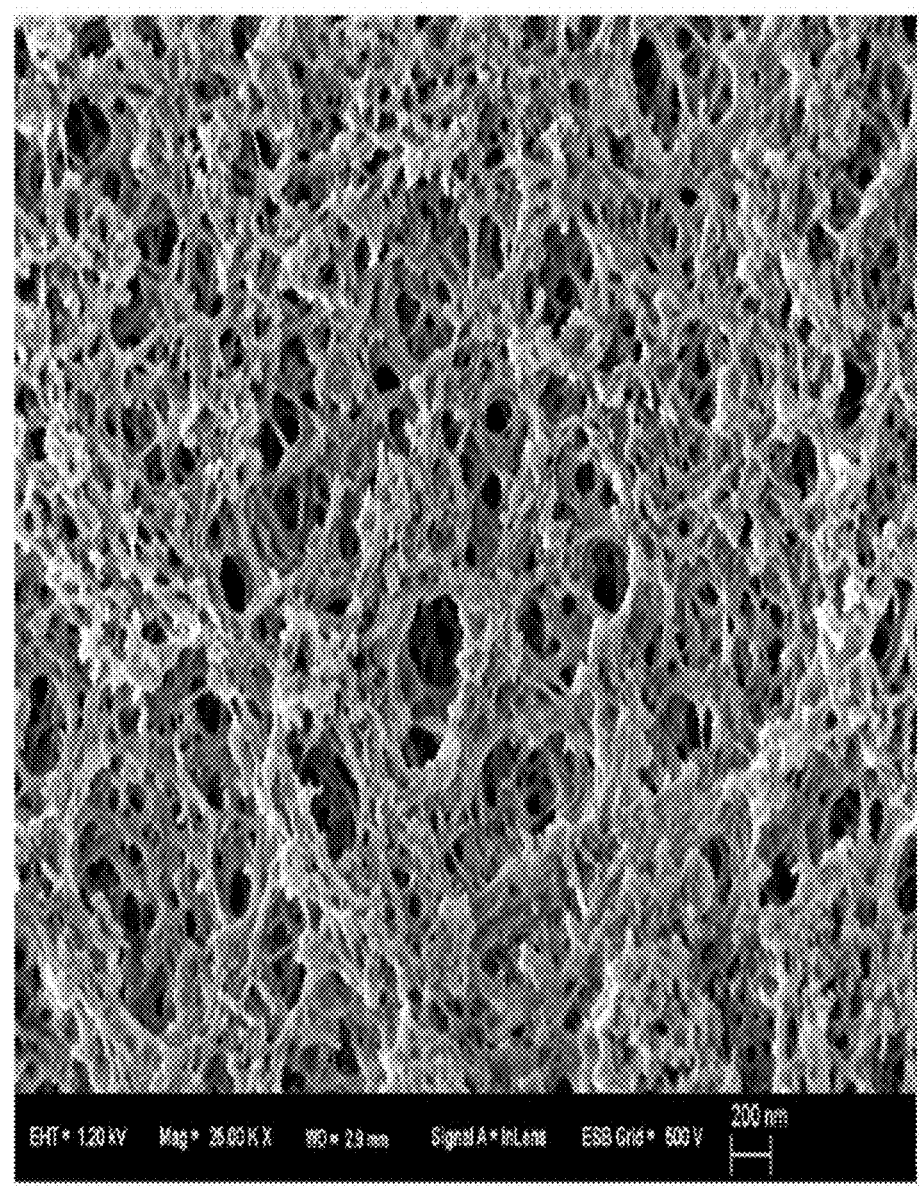

[Fig. 7]
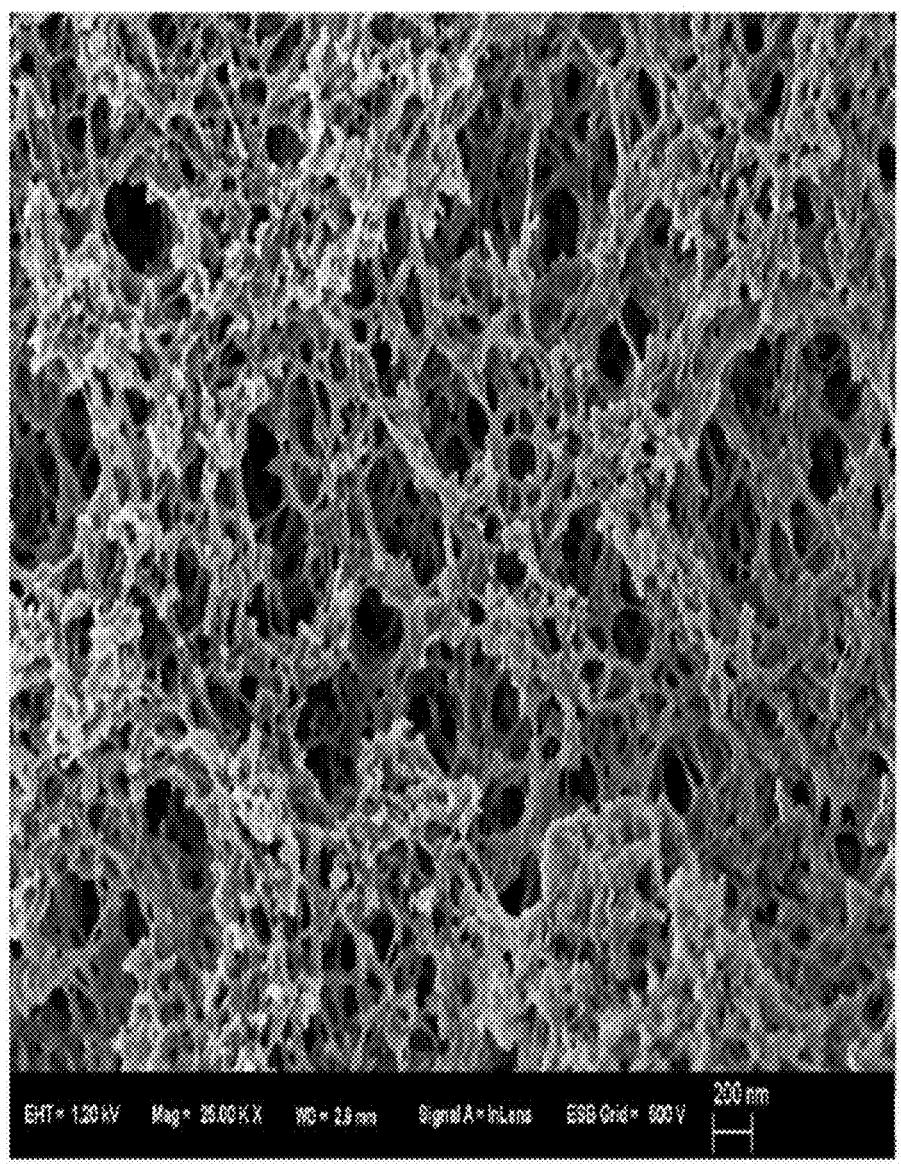

PRODUCTION METHOD FOR POROUS CELLULOSE BEADS, AND ADSORBENT EMPLOYING SAME

TECHNICAL FIELD

The present invention relates to a method for producing porous cellulose beads and an adsorbent which contains the porous cellulose beads. More specifically, the present invention relates to a method for producing high-performance porous cellulose beads which can be used for producing an adsorbent of which adsorption amount is large and which is excellent in strength, and the adsorbent itself.

BACKGROUND ART

An adsorbent which is produced from porous cellulose beads has the advantages of being safer, exhibiting smaller non-specific adsorption, and being used in broader pH range in comparison with adsorbent produced from other synthetic polymers. In addition, such an adsorbent also has the advantage of having larger mechanical strength, though cellulose is a polysaccharide.

As a use application of an adsorbent which is produced from porous cellulose beads, various medical adsorbents, an adsorbent for chromatography and an affinity adsorbent are exemplified. Among the examples, an affinity adsorbent is used as a medical adsorbent and an adsorbent for purifying a medical antibody, since a target substance can be purified and an undesired substance amount can be reduced efficiently by using an affinity adsorbent. In particular, as a medical adsorbent for treating rheumatism, hemophilia or dilated cardiomyopathy, an adsorbent produced by immobilizing Protein A as an affinity ligand on a porous carrier has attracted attention (for example, Non-patent document 1 and Non-patent document 2).

In addition, it has attracted attention that an adsorbent produced by immobilizing Protein A as an affinity ligand on a porous carrier is used as an adsorbent for purifying a medical antibody by specifically adsorbing an immune globulin, i.e. IgG.

In recent years, since a purification scale has become larger with increasing need for a medical antibody, an adsorbent by which purification at high speed becomes possible and which is produced from porous cellulose beads, in other words, an adsorbent which is produced from porous cellulose beads having high strength, has been required. Under such circumstances, the present inventors filed a patent application by finding that the strength of porous carrier can be enhanced by treating the porous carrier with a long-chain crosslinking agent which has two or more functional groups.

However, when an amount of solid content is increased in order to enhance the strength only, an adsorption amount may be possibly decreased. Accordingly, high-performance porous cellulose beads suitable for producing an adsorbent of which mechanical strength is high and of which adsorption amount is large are required.

PRIOR ART DOCUMENT

Patent Document

Patent Document 1: JP 2011-252929 A

Non-Patent Document

Non-patent Document 1: Annals of the New York Academy of Sciences, 2005, Vol. 1051, p. 635-646

Non-patent Document 2: American Heart Journal, Vol. 152, Number 4, 2006

DISCLOSURE OF THE INVENTION

Problems to be Solved by the Invention

The objective of the present invention to solve the above-described problem of prior arts is to provide a method for easily producing high-performance porous cellulose beads having high mechanical strength. Also, the objective of the present invention is to provide an adsorbent produced from the high-performance porous cellulose beads.

Means for Solving the Problems

The inventors of the present invention made extensive studies to solve the above problems. As a result, the inventors completed the present invention by finding that the strength of crosslinked porous cellulose beads can be surprisingly maintained or enhanced by treating with a cellulolytic enzyme and an adsorption amount of an adsorbent produced by immobilizing an affinity ligand on the treated beads can be remarkably increased.

Hereinafter, the present invention is described.

[1] A method for producing high-performance porous cellulose beads, comprising the step of treating crosslinked cellulose beads with a cellulolytic enzyme.

[2] The method for producing high-performance porous cellulose beads according to the above [1], wherein an endo-type cellulolytic enzyme is used as the cellulolytic enzyme.

[3] The method for producing high-performance porous cellulose beads according to the above [2], wherein an exo-type cellulolytic enzyme is further used as the cellulolytic enzyme.

[4] The method for producing high-performance porous cellulose beads according to any one of the above [1] to [3], wherein the crosslinked cellulose beads are treated with the cellulolytic enzyme for not less than 1 hour and not more than 10 hours.

[5] The method for producing high-performance porous cellulose beads according to any one of the above [1] to [4], wherein the crosslinked cellulose beads are crosslinked by a glycidyl ether-type compound as a crosslinking agent.

[6] The method for producing high-performance porous cellulose beads according to any one of the above [1] to [5], wherein the crosslinked cellulose beads are crosslinked using water as a reaction solvent for a crosslinking reaction.

[7] A method for producing an adsorbent, comprising the step of immobilizing a ligand interacting with a target substance to be adsorbed on the high-performance porous cellulose beads produced by the method according to anyone of the above [1] to [6] to obtain the adsorbent.

[8] An adsorbent, comprising the high-performance porous cellulose beads produced by the method according to any one of the above [1] to [6] and a ligand interacting with a target substance to be adsorbed.

[9] An adsorbent, produced by immobilizing a ligand interacting with a target substance to be adsorbed on the high-performance porous cellulose beads produced by the method according to any one of the above [1] to [6].

[10] A purification method, comprising the step of contacting the adsorbent according to the above [8] or [9] with a solution containing the target substance to be adsorbed.

Effect of the Invention

According to the present invention, high-performance porous cellulose beads can be produced without difficulty from porous cellulose beads. In addition, an adsorbent having high strength and large adsorption amount can be easily produced from the high-performance porous cellulose beads.

BRIEF DESCRIPTION OF THE DRAWINGS

FIG. 1 is a photograph of the surface of the uncrosslinked cellulose beads of Production example 1 according to the present invention.

FIG. 2 is a photograph of the surface of the crosslinked cellulose beads of Production example 1 according to the present invention.

FIG. 3 is a photograph of the surface of the high-performance porous cellulose beads of Example 1 according to the present invention.

FIG. 4 is a photograph of the surface of the crosslinked cellulose beads of Production example 2 according to the present invention.

FIG. 5 is a photograph of the surface of the high-performance porous cellulose beads of Example 2 according to the present invention.

FIG. 6 is a photograph of the torn surface of the crosslinked cellulose beads of Production example 3 according to the present invention.

FIG. 7 is a photograph of the torn surface of the high-performance porous cellulose beads of Example 3 according to the present invention.

MODE FOR CARRYING OUT THE INVENTION

The method for producing high-performance porous cellulose beads according to the present invention is characterized in comprising the step of treating cross linked porous cellulose beads with a cellulolytic enzyme. As the crosslinked porous cellulose beads and a porous cellulose which is a precursor thereof, a commercial product may be used. Alternatively, the porous celluloses may be produced from cellulose. Hereinafter, the present invention method in addition to the step for producing crosslinked porous cellulose beads from cellulose is described step by step.

1. Step for Producing Porous Cellulose Beads

In the present step, porous cellulose beads are obtained by adding a coagulating solvent to a cellulose emulsion.

In the present invention, the term "cellulose emulsion" means a dispersion in which droplets containing cellulose are dispersed in an oil-soluble solvent. The droplet containing cellulose may be a cellulose dispersion or a cellulose solution.

A solvent of a cellulose dispersion is exemplified by a basic aqueous solution such as a sodium hydroxide aqueous solution. Cellulose can be dispersed in a basic aqueous solution even if cannot be dissolved, since cellulose is difficult to be dissolved but is hydrophilic and has many hydroxy groups. A solvent of a cellulose solution is exemplified by an ion liquid such as 1-ethyl-3-methylimidazolium acetate. A cellulose powder is preferably used as a raw material cellulose, since it is easy to disperse or dissolve a cellulose powder.

As an oil-soluble solvent of a cellulose emulsion, an animal and plant fat and oil, a hydrogenated animal and plant fat and oil, a fatty acid triglyceride, an aliphatic hydrocarbon solvent and an aromatic hydrocarbon solvent are exemplified. In addition, a surfactant such as a non-ionic surfactant may be used.

A cellulose emulsion may be prepared by an ordinary method. For example, a cellulose emulsion can be prepared by vigorously stirring a mixed liquid which contains a cellulose dispersion or cellulose solution, a lipophilic solvent and a surfactant.

In the present step, porous cellulose beads are obtained by adding a coagulating solvent to a cellulose emulsion to remove the solvent from cellulose droplets. It is preferred to add the coagulating solvent with vigorously stirring the cellulose emulsion in order not to bind droplets each other, since the cellulose emulsion is sometimes unstable.

The coagulating solvent is not particularly restricted as long as the solvent has an affinity for the solvent of the dispersion or solution of cellulose, and is exemplified by an alcohol and an alcohol aqueous solution. Such an alcohol is exemplified by $C_{1-4}$ alcohol such as methanol, ethanol, n-propanol, isopropanol, n-butanol, isobutanol, s-butanol and t-butanol. For example, a ratio of water and alcohol in an alcohol aqueous solution may be adjusted to water: alcohol=80:20 to 5:95 by volume.

After the coagulating solvent is added, coagulated porous cellulose beads may be isolated by a means such as filtration and centrifugation, and then washed by water, an alcohol and the like. The obtained porous cellulose beads may be classified using a sieve or the like in order to control the particle size to be uniform.

As described above, commercially available porous cellulose beads may be used, and the present step may be carried out or may not be carried out.

2. Step for Crosslinking Porous Cellulose Beads

In the present step, porous cellulose beads are crosslinked by a crosslinking agent to obtain crosslinked porous cellulose beads.

The crosslinking agent has two or more reactive groups which are able to covalently bind to the hydroxy group on a cellulose so as to crosslink cellulose molecules. The crosslinking condition and crosslinking agent in the present invention for crosslinked porous cellulose beads are not particularly restricted. For example, the method described in WO 2008/146906 can be used.

However, the present inventors found that more remarkable effect can be sometimes obtained by crosslinking the above-described porous cellulose beads with a glycidyl ether compound. Specifically, in particular, when crosslinking reaction is carried out at a high level with using a crosslinking agent having high molecular weight and/or many functional groups, the pore on the surface of porous cellulose beads may be possibly closed. In such a case, when a glycidyl ether compound is used as a crosslinking agent, the pore on the surface of the beads may be maintained. In addition, in the case, the strength of the beads is not lowered though the beads are treated with a cellulolytic enzyme.

The glycidyl ether compound to be used as a crosslinking agent, i.e. a glycidyl ether crosslinking agent, is preferably exemplified by resorcinol diglycidyl ether, neopentyl glycol diglycidyl ether, 1,6-hexanediol diglycidyl ether, hydrogenated bisphenol A diglycidyl ether, glycerol diglycidyl ether, trimethylolpropane diglycidyl ether, diglycidyl terephthalate, diglycidyl ortho-phthalates, ethylene glycol diglycidyl ether, diethylene glycol diglycidyl ether, propylene glycol diglycidyl ether, glycerol polyglycidyl ether, trimethylolpropane polyglycidyl ether, pentaerythritol polyglycidyl ether, diglycerol polyglycidyl ether, polyglycerol polyglycidyl ether and sorbitol polyglycidyl ether.

Only one crosslinking agent may be used alone, or two or more crosslinking agents may be used in combination. For example, a glycidyl ether crosslinking agent may be mixed with other crosslinking agent such as epichlorohydrin to be used.

The solvent used in the reaction for crosslinking porous cellulose beads by a crosslinking agent may be appropriately selected, and is exemplified by a water-miscible organic solvent in addition to water. The example of such a water-miscible organic solvent includes an alcohol solvent such as methanol, ethanol and isopropanol, and a nitrile solvent such as acetonitrile. Two or more solvents may be mixed to be used for the crosslinking reaction.

When a glycidyl ether crosslinking agent is used, high-performance porous cellulose beads having improved strength may be sometimes obtained, even though a cellulolytic enzyme is used. Such beads may be obtained more readily when the solvent of the reaction for crosslinking the above-described cellulose beads is water and the above-described glycidyl ether crosslinking agent is used for the crosslinking. The phrase "the solvent of the reaction for crosslinking is water" means that the volume of water in the composition of the liquid part of the reaction mixture is not less than 50%. The ratio is preferably not less than 60%, not less than 70% or not less than 80%, more preferably not less than 90%, and particularly preferably not less than 95%.

The crosslinking reaction may be carried out multiple times, and the reaction solvent and the crosslinking agent may be changed in each time. For example, a first crosslinking reaction may be carried out in a water-miscible organic solvent, and a final crosslinking reaction may be carried out in water. In such a case, the solvent compositions from second to second last reactions may be the same as or different from that of a first reaction or a last reaction, or an intermediate composition between those of a first reaction and a last reaction. Alternatively, all of the reactions may be carried out in water. The conditions are also applied to the crosslinking agent. When the crosslinking reaction is carried out multiple times, it is preferred to use water as all of the reaction mixture, since the remarkable effect can be obtained by using water as the reaction mixture. When the crosslinking reaction is carried out multiple times, it is preferred that the crosslinked porous cellulose is washed with water or the like between the crosslinking reactions.

A base may be added to the reaction mixture in order to accelerate the crosslinking reaction. Such a base is exemplified by an alkali metal hydroxide such as sodium hydroxide and potassium hydroxide; an alkali metal hydrogencarbonate salt such as sodium hydrogencarbonate and potassium hydrogencarbonate; an alkali metal carbonate salt such as sodium carbonate and potassium carbonate; an organic base such as triethylamine and pyridine.

After the crosslinking reaction, the crosslinked porous cellulose beads may be washed with water, since the beads is insoluble.

As described above, a commercially available crosslinked porous cellulose beads may be used and the present step may be carried out or may not be carried out. However, the present step is preferably carried out, since high-performance porous cellulose beads having good properties can be obtained by using a glycidyl ether crosslinking agent as the crosslinking agent or using water as the solvent for the crosslinking reaction.

3. Step of Treating with Cellulolytic Enzyme

In the present step, high-performance porous cellulose beads are obtained by treating the crosslinked porous cellulose beads with a cellulolytic enzyme.

The high-performance porous cellulose beads according to the present invention are produced by treating crosslinked porous cellulose beads with a cellulolytic enzyme, and has high strength. In addition, when the high-performance porous cellulose beads are used, an adsorbent of which adsorption amount is large can be obtained. Even though the high-performance porous cellulose beads according to the present invention are produced by the treatment with a cellulolytic enzyme, the strength before the treatment is surprisingly maintained. However, the reason is unknown.

The present inventors found that the adsorption amount of the adsorbent produced from the high-performance porous cellulose beads is larger than that produced without using a cellulolytic enzyme. The present inventors consider the reason is that an uncrosslinked glucose unit may be separated from the cellulose molecule in the high-performance porous cellulose beads by a cellulolytic enzyme, and a micropore volume in the porous cellulose beads becomes larger; as a result, the adsorption amount of the adsorbent produced from the high-performance porous cellulose beads may become larger by increasing the site to be adsorbed by a target substance. In addition, the reason why the strength of the beads are maintained is conceivably that the crosslinked glucose unit is not recognized as a substrate by a cellulolytic enzyme or is kept bound to the cellulose molecule even if the unit is attacked by a cellulolytic enzyme.

The cellulolytic enzyme used in the present invention is not particularly restricted, and is exemplified by an end-type cellulolytic enzyme such as endo-β-1,4-glucanase and carboxymethylcellulase; and an exo-type cellulolytic enzyme such as exo-β-1,4-glucanase.

In the present invention, it is considered that the cellulolytic enzyme selectively attacks uncrosslinked glucose unit. An endo-type cellulolytic enzyme randomly treats cellulose to produce cellodextrin, cellobiose and glucose. As a result, when an endo-type cellulolytic enzyme is used, the high-performance porous cellulose beads of which strength is maintained but of which micropore volume is increased can be produced more readily by liberating such a glucose unit, even if uncrosslinked glucose unit exists at the part other than the terminals of cellulose molecule.

An exo-type cellulolytic enzyme generally cleaves a cellulose molecule by a cellobiose unit from the terminal. Also, an exo-type cellulolytic enzyme is preferably used, since the degradation activity of an exo-type cellulolytic enzyme is considered to be higher than that of an endo-type cellulolytic enzyme against uncrosslinked cellulose and a glucose unit at the terminal of a cellulose molecule is sometimes uncrosslinked.

Only one of the cellulolytic enzyme may be used alone, or two or more cellulolytic enzymes may be used in combination. For example, a mixture of an endo-type cellulolytic enzyme and an exo-type cellulolytic enzyme may be used. In addition, β-glucosidase, which decomposes cellobiose to glucose, may be used. There is also a cellulolytic enzyme which acts as both an endo-type and an exo-type.

The origin of a cellulolytic enzyme is not particularly restricted, and a natural cellulase derived from a higher plant, bacteria, filamentous fungus, wood rotting fungus, a protozoan symbiotically living with termite, and the like may be used or an artificial cellulase produced by a genetic engineering procedure may be used. The origin of a cellulase is preferably exemplified by *Trichoderma* fungus, *Aspergillus* fungus, *Humicol* fungus, *Staphylotrichum* fungus, *Rhizopus* fungus, *Mucor* fungus, *Acremonium* fungus, *Chaetomium* fungus, *Acidothermus* fungus and *Cellulomonas* fungus. In terms of availability, *Aspergillus* fungus and *Trichoderma* fungus are more preferred, and *Aspergillus* fungus is the most preferred.

An amount of the cellulolytic enzyme to be used according to the present invention is not particularly restricted, and for example, when a specific activity of an enzyme product is not less than 20000 u/g and not more than 30000 u/g, particularly 22900 u/g, the amount is preferably not less than 0.01 g per 1 g of the beads in a wet condition. In addition, the amount is preferably not more than 10 g per 1 g of the beads in a wet condition in terms of washing efficiency after the enzyme reaction and cost. The amount is more preferably not less than 0.1 g and not more than 5 g, even more preferably not less than 0.2 g and not more than 1 g, most preferably not less than 0.5 g and not more than 0.8 g. In the present invention, the term "beads in a wet condition" means beads prepared by filtrating a slurry of beads to remove an excessive solvent around the beads.

As the solvent of the enzyme reaction, water is generally used.

In the present invention, the value of pH of the reaction mixture for the treatment with the cellulolytic enzyme is not particularly restricted, and is preferably not less than 2 and not more than 7 in terms of efficient acceleration of the enzyme reaction. The value of pH is more preferably not less than 3 and not more than 6, even more preferably not less than 4 and not more than 5.5, and particularly preferably not less than 4.5 and not more than 5.1. The method for adjusting the pH is not particularly restricted, but it is preferred to use a compound having pH buffering action. Such a compound having pH buffering action is not particularly restricted, and is exemplified by acetic acid, an acetate salt, citric acid, a citrate salt, phosphoric acid, a phosphate salt, carbonic acid, a carbonate salt and the like. One or more compounds among the examples are preferably used. A use amount of the compound having pH buffering action is not particularly restricted, and is preferably not less than 0.01 wt % of the reaction mixture in terms of suppression of pH change. The amount is also preferably not more than 50 wt % in terms of cost. The amount is more preferably not less than 0.05 wt % and not more than 10 wt %, and even more preferably not less than 0.1 wt % and not more than 5 wt %.

The temperature of the reaction mixture when the cellulolytic enzyme is reacted is not particularly restricted, and is preferably not less than 0° C. and not more than 100° C. in order to efficiently accelerate the reaction. The temperature is more preferably not less than 10° C. and not more than 80° C., even more preferably not less than 25° C. and not more than 70° C., particularly preferably not less than 35° C. and not more than 60° C., and most preferably not less than 40° C. and not more than 55° C.

The time for reacting the cellulolytic enzyme is not particularly restricted, and is preferably not less than 1 minute in terms of high reaction efficiency and not more than 48 hours in terms of production efficiency. The reaction time is more preferably not less than 10 minutes, even more preferably not less than 30 minutes, particularly preferably not less than 1 hour, and more preferably not more than 24 hours, even more preferably not more than 12 hours, particularly preferably not more than 6 hours, and most preferably not more than 3 hours. In particular, when the reaction time is not less than 1 hour, the high-performance porous cellulose from which adsorbent having maintained strength and high adsorption performance can be obtained more certainly. When the reaction time is not more than 10 hours, the strength of the high-performance porous cellulose beads can be maintained more surely.

By the present step, the high-performance porous cellulose beads are obtained by the treatment with the cellulolytic enzyme; none the less, the strength thereof is maintained or improved in comparison with the raw material crosslinked porous cellulose beads. In addition, when an adsorbent is obtained by immobilizing an affinity ligand on the high-performance porous cellulose beads, the adsorbent exhibits an excellent adsorption capacity against a target substance to be adsorbed. For example, the strength as a guide of the high-performance porous cellulose beads according to the present invention is not less than about 0.03 MPa and not more than about 0.4 MPa as a 20% compressive stress. The strength is preferably not less than about 0.08 MPa and not more than about 0.3 MPa. The term "20% compressive stress" means a stress of beads when the beads are compressed so that the sedimentation volume of the beads is reduced by 20%.

4. Step of Immobilizing Ligand

The high-performance porous cellulose beads according to the present invention has high strength. In addition, when a ligand which interacts with a target substance to be adsorbed is immobilized on the high-performance porous cellulose beads to obtain an adsorbent, the adsorption capacity of the adsorbent against the target substance to be adsorbed is excellent. In the present step, an adsorbent is obtained by immobilizing a ligand on the high-performance porous cellulose beads according to the present invention.

In the present invention, the term "ligand" means an affinity ligand which has a specific affinity for a target substance to be adsorbed and which interacts with the target substance to be adsorbed. For example, when a target substance to be adsorbed is an antibody, a ligand is exemplified by an antigen, a protein, a peptide fragment and the like which specifically interact with the antibody. The ligand used for the adsorbent according to the present invention is not particularly restricted as long as the ligand has a specific affinity for a target substance which should be adsorbed and which should be purified using the adsorbent according to the present invention.

A method for immobilizing a ligand on the high-performance porous cellulose beads according to the present invention is not particularly restricted, and an ordinary method may be used. For example, various immobilization methods are exemplified, such as a method for immobilizing an amino group-containing ligand using a cyanogen bromide method, a trichlorotriazine method, an epoxy method, a tresyl chloride method, a periodic acid oxidation method, a divinylsulfonic acid method, a benzoquinone method, a carbonyldiimidazole method, an acyl azide method or the like; a method for immobilizing a hydroxy group-containing ligand using an epoxy method, a diazo coupling method or the like; a method for immobilizing a thiol group-containing ligand using an epoxy method, a tresyl chloride method, a divinylsulfonic acid method or the like; a method for immobilizing a carboxy acid group-containing ligand and a formyl group-containing ligand on an aminated carrier, as described in Kenichi KASAI et al., "Affinity chromatography" published by Tokyo Kagakudoujin, 1991, Table 8-1, Table 8-2 and FIG. 8-15. The contents of the document are incorporated by reference herein.

The adsorbent according to the present invention can be used as an adsorbent for purification, particularly as an adsorbent for purifying an antibody pharmaceutical which has attracted attention in recent years. An ligand used for an adsorbent for purifying an antibody pharmaceutical is not particularly restricted, and is exemplified by an amino group-containing ligand such as an antigen and a protein which have specific affinity for an antibody; Protein A, Protein G, Protein L, and variants thereof; and a peptide having an antibody binding activity.

In particular, an adsorbent which is prepared by immobilizing Protein A, Protein G or a variant thereof as a ligand on a porous carrier has attracted attention as an adsorbent capable specifically adsorbing an immunoglobulin, i.e. IgG. The above-described Protein A used in the present invention is not particularly restricted, and natural Protein A, transgenic Protein A and the like may be used without restriction. In addition, a substance containing an antibody-binding domain, a variant thereof or an oligomer thereof, a fused protein and the like may be used. The polymerization number of such an oligomer may be not less than 2 and not more than 10. In addition, Protein A and the like to be used can be produced from an extract obtained from fungus body or a culturing supernatant by combining and/or repeating a purification method selected from a molecular weight fractionation, a fractional precipitation and the like in which various chromatography and membrane separation technique are utilized. Such a chromatography is exemplified by ion-exchange chromatography, hydrophobic interaction chromatography, gel filtration chromatography and hydroxyapatite chromatography. In particular, it is preferred that Protein A is obtained by the method described in WO 2006/004067, U.S. Pat. No. 5,151,350, WO 2003/080655, JP 2006-304633 A and WO 2010/110288. The contents described in the publications are incorporated by reference. The adsorbent according to the present invention on which Protein A is immobilized can be also utilized as an adsorbent used for treating dilated cardiomyopathy and the like. In addition, the adsorbent according to the present invention on which dextran sulfate and the like is immobilized can be utilized as an adsorbent used for treating hypercholesterolemia.

A method for introducing a ligand in the high-performance porous cellulose beads may be selected from the above-described immobilization methods, and it is more preferred that a reaction between a formyl group that a porous particle has and an amino group of a ligand is utilized to carry out immobilization. For example, the method described in JP H1-278534 A is used. All of the contents of the publication are incorporated by reference herein.

An amount of the ligand to be immobilized in the adsorbent according to the present invention is not particularly restricted, and for example, may be adjusted to not less than 1 mg and not more than 1000 mg per 1 mL of the high-performance porous cellulose beads. When the ratio is 1 mg or more, an adsorption amount of a target substance to be adsorbed preferably becomes large. When the ratio is 1000 mg or less, the production cost may be preferably reduced. An amount of the ligand to be immobilized per 1 mL of the high-performance porous cellulose beads is more preferably not less than 2 mg, even more preferably not less than 4 mg, particularly preferably not less than 5 mg, and more preferably not more than 500 mg, even more preferably not more than 250 mg, particularly preferably not more than 200 mg, most preferably not more than 100 mg.

The adsorbent according to the present invention is obtained from the high-performance porous cellulose beads produced by the present invention method. The method for evaluating the strength of the high-performance porous cellulose beads and adsorbent is not particularly restricted, and the strength may be evaluated by the measurement of a compressive stress as described in Test example 2 described later.

By the present invention, the effects that the surface porosity of the porous cellulose beads is improved and the adsorption amount of the adsorbent obtained from the beads becomes larger while the strength is maintained or improved can be obtained by the very simple method in which crosslinked cellulose beads are treated with a cellulolytic enzyme. The use application of the adsorbent is not particularly restricted, and the adsorbent is preferably used as a medical adsorbent. In particular, the adsorbent is preferably used as a therapeutic adsorbent for adsorbing a large-sized disease substance such as LDL cholesterol to be removed, since the surface porosity of the adsorbent is improved. In addition, the adsorbent can be used as various chromatographic carriers, particularly as an industrial chromatographic carrier which is used for filling a large-diameter column. In particular, when the adsorbent is used as an adsorbent for purifying an antibody pharmaceutical, of which demand has been very heavy recently, the effect of the adsorbent can be exhibited. In terms of the above points, the high-performance porous cellulose beads according to the present invention are preferably used for producing an adsorbent in which Protein A, Protein G or Protein L is immobilized.

In order to purify a target substance to be adsorbed by using the adsorbent according to the present invention, the adsorbent is brought contact with a solution of the target substance to be adsorbed. A contacting method is not restricted, and the adsorbent according to the present invention may be added to a solution which contains a target substance to be adsorbed, or a target substance to be adsorbed may be selectively adsorbed on the adsorbent according to the present invention by filling a column with the present invention adsorbent as described above and flowing a solution containing the target substance through the column. In particular, when a column is filled with the present invention adsorbent, a solution can be flowed at high speed so that a target substance to be adsorbed can be efficiently purified, since the strength of the present invention adsorbent is high.

Next, the present invention adsorbent on which a target substance to be adsorbed is selectively adsorbed is separated from a solution by filtration, centrifugation or the like. By such a step, a target substance to be adsorbed can be separated from other substances. In addition, a target substance to be adsorbed is separated from the present invention adsorbent by using an eluate. As such an eluate, for example, an acidic buffer solution of which pH value is not less than about 2.5 and not more than about 4.5 may be used.

The present application claims the benefit of the priority date of Japanese patent application No. 2013-215119 filed on Oct. 15, 2013. All of the contents of the Japanese patent application No. 2013-215119 filed on Oct. 15, 2013, are incorporated by reference herein.

EXAMPLES

Hereinafter, the present invention is described in more detail with Examples. However, the present invention is not restricted to the following Examples in any way.

Test Example 1: Observation Using Scanning Electron Microscope (SEM)

The beads obtained in each Production example and Example were washed with 30% ethanol of five times amount by volume in order to replace the liquid part included in the beads by 30% ethanol. Then, the beads were similarly treated with 50% ethanol, 70% ethanol, 90% ethanol, special grade ethanol, special grade ethanol and special grade ethanol in turns in order to replace the liquid part by ethanol. Further, the beads were similarly treated by a mixed solvent of t-butyl alcohol/ethanol=3/7. Next, the beads were treated by mixed solvents of t-butyl alcohol/ ethanol=5/5, 7/7, 9/1, 10/0, 10/0 and 10/0 in turns in order to replace the liquid part by t-butyl alcohol, and then freeze-dried. In the case of surface observation, the freeze-dried beads were subjected to deposition treatment of which deposition source was gold/palladium, and SEM observation image was photographed using a scanning electron microscope ("S-800" manufactured by Hitachi, Ltd.). In the case of torn surface observation, SEM observation image was photographed using a scanning electron microscope ("ULTRAplus" manufactured by CarlZeiss), after the freeze-dried beads were torn to expose the inside of the beads and subjected to deposition treatment of which deposition source was osmium tetrachloride crystal.

Test Example 2: Measurement of 20% Compression Stress (1) Preparation of Sample

Pure water was added to sample beads to prepare a slurry of which concentration was about 50 vol %. The slurry was homogenized by stirring and then deaerated under reduced pressure for 30 minutes or more. The homogenization and deaeration procedure was repeated 3 times to obtain a deaerated slurry. Separately, the processed object was changed to pure water and the above homogenization and deaeration procedure was carried out for 90 minutes or more to obtain deaerated water.

(2) Preparation of Beads-Filled Syringe

A disposable filter (manufactured by Sartorius, pore diameter: 5.00 μm, hydrophilic) was attached to the tip of 5 mL disposable syringe with a lure lock (Product name: NORM-JECT, manufactured by HANKE SASS WOLF). The piston was removed from the syringe, about 3 mL of deaerated water was added from the rear end side of the syringe, and the deaerated slurry was added before the added deaerated water fell below the gauge line of 0 mL. An aspirator was connected to the secondary side of the disposable filter to aspirate the above-described deaerated slurry. The suction was stopped when the liquid level was decreased to about 0.5 mL in addition to the volume of the precipitated beads so that the beads were not dried by the suction. The subsequent procedures were carried out with adding pure water which was deaerated by reduced pressure so that the liquid level did not fall below 0.5 mL in addition to the volume of the precipitated beads. The height of the beads as filler was adjusted to the gauge line of 3 mL by adding the above-described deaerated slurry or removing the beads with giving vibration until it was confirmed that the height of the beads as filler was not decreased anymore even when vibration was given. Deaerated water was slowly added so that the beads were not flied up until deaerated water overflowed, and then the piston was inserted carefully not to mix air bubbles. Hereinafter, the obtained syringe is referred to as "beads-filled syringe".

(3) Measurement

A 10 K load cell was installed on a physical property measuring instrument ("FUDOH RHEO METER" manufactured by RHEOTECH), the dial of displacement speed was set at 2 cm/MIN, and the above-described beads-filled syringe was placed. Then, the displacement of the piston was started. The relationship between the displacement and the stress was recorded, and 20% compression stress was calculated according to the following formula.

20% Compression stress=(Stress when filling beads was pressed by 20%)−(Stress just before piston reaches beads surface)

Test Example 3: Measurement of Dynamic Adsorption Amount at RT (Residence Time) of 3 Minutes (1) Preparation of Solutions The following Liquids A to E and a neutralizing liquid were prepared and deaerated before use.

Liquid A: phosphate buffered saline with a pH of 7.4, prepared from "Phosphate buffered saline" manufactured by SIGMA and water purified using an osmosis membrane, i.e. RO water Liquid B: 35 mM sodium acetate aqueous solution with a pH of 3.5, prepared from acetic acid, sodium acetate and RO water Liquid C: 1 M acetic acid aqueous solution prepared from acetic acid and RO water Liquid D: IgG aqueous solution having a concentration of 1 mg/mL, prepared from polyclonal antibody ("Gammagard" manufactured by Baxter) and the above-described Liquid A Liquid E: 6 M urea aqueous solution prepared from urea and RO water Neutralizing liquid: 2 M tris(hydroxymethyl)aminomethane aqueous solution prepared from tris(hydroxymethyl) aminomethane and RO water (2) Filling and Preparation An adsorbent obtained by immobilizing a ligand on crosslinked beads was used as a sample. As a mobile phase, 0.2 M NaCl aqueous solution prepared by adding NaCl to RO water was used. As a column chromatography apparatus, AKTAexplorer100 manufactured by GE Healthcare was used. Into a column having a diameter of 0.5 cm and height of 15 cm, 3 mL of the adsorbent sample was added. The column was filled with the adsorbent sample by flowing 0.2 M NaCl aqueous solution at a linear speed of 230 cm/h for 15 minutes. On a fraction collector, 15 mL correcting tubes were set. In the correcting tube for an eluent, Neutralizing liquid was preliminarily added.

(3) Purification of IgG

Through the above-described column, 15 mL of Liquid A was flowed and then 150 mL of Liquid D was flowed. Next, after 21 mL of Liquid A was flowed, 12 mL of Liquid B was flowed to elute IgG. Then, 6 mL of Liquid C, 6 mL of Liquid E and 15 mL of Liquid A were flowed. The flow speed of each liquid was adjusted to 1 mL/min so that the time of contact between the adsorbent and each liquid was 3 minutes.

(4) Dynamic Adsorption Amount

A dynamic adsorption amount of IgG at RT of 3 minutes was calculated from the volume of the adsorbent and the amount of IgG which was adsorbed on the adsorbent by 5% of IgG was passed through. Hereinafter, the dynamic adsorption amount is abbreviated to "5% DBC".

Production Example 1: Preparation of Crosslinked Porous Cellulose Beads (1) Preparation of Alkaline Aqueous Solution Using sodium hydroxide manufactured by Wako Pure Chemical Industries, Ltd. and pure water, 33 wt % sodium hydroxide aqueous solution was prepared. The temperature thereof was adjusted to 4° C.

(2) Preparation of Cellulose Dispersion

Were mixed 76 g of powdery cellulose ("pharmacopoeia cellulose PH-F20JP" manufactured by Asahi Kasei Chemicals Corporation) and 800 g of pure water, and the temperature of the obtained mixture was adjusted to 4° C. with stirring. Then, 400 g of the above-described alkaline aqueous solution of which temperature was adjusted to 4° C. was added thereto while the set temperature and stirring were maintained, and the mixture was stirred for 30 minutes.

(3) Preparation of Porous Cellulose Beads

Were mixed 1276 g of the cellulose dispersion of which temperature was adjusted to 4° C., 7801 g of ortho-dichlorobenzene of which temperature was adjusted to 4° C. and 78 g of solbitan monooleate which was corresponds to span80 and of which temperature was adjusted to 4° C., and the mixture was stirred in a stainless steel vessel with two Rushton turbines and a temperature control jacket at 460 rpm, Pv value of 5.0 kW/m$^3$ and 4° C. for 15 minutes to prepare an emulsion. Then, 592 g of methanol of which temperature was adjusted to 4° C. was added as a coagulating solvent thereto while the set temperature and stirring were maintained. The time required for adding the coagulating solvent was 5 seconds. Next, the mixture was stirred for 30 minutes while the stirring rate and set temperature were maintained. After the mixture was filtered under pressure, washing procedure using 3000 g of methanol and then 3000 g of water was carried out to obtain porous cellulose beads. It was confirmed that the obtained porous cellulose beads had preferred pores on the surface as FIG. 1.

(4) Preparation of Crosslinked Porous Cellulose Beads

The obtained porous cellulose beads were subjected to wet classification using sieves of 38 μm and 90 μm, and then a slurry of the porous cellulose beads having a volume of 20 mL as a beads volume and water was added into a reaction vessel. After the beads were naturally settled out, excessive water was removed to adjust the liquid volume to 22 mL. To the slurry, 22 mL of a crosslinking agent solution prepared by mixing glycerol polyglycidyl ether ("Denacol EX-314" manufactured by Nagase ChemteX Corporation) and acetonitrile in a volume ratio of 1:1 was added. The mixture was stirred overnight.

The mixture was filtered on a glass filter. To the obtained beads, 22 mL of the above-described crosslinking agent solution was added to be filtered again. The beads were transferred into a reaction vessel, and the liquid amount was adjusted to 22 mL by adding the above-described crosslinking agent solution. Then, 18 mL of 2 M sodium hydroxide aqueous solution prepared from pure water and sodium hydroxide manufactured by Wako Pure Chemical Industries, Ltd. was added thereto. The mixture was stirred at 40° C. for 10 minutes. Next, 7.6 g of sodium sulfate decahydrate manufactured by Wako Pure Chemical Industries, Ltd. and 3 mL of glycerol polyglycidyl ether ("Denacol EX-314" manufactured by Nagase ChemteX Corporation) were added thereto. The mixture was stirred at 40° C. for 4 hours and 50 minutes. After the mixture was filtered, the obtained beads were washed with large amount of pure water to obtain first crosslinked beads. The slurry of the obtained first crosslinked beads and water was added into a reaction vessel. After the beads were naturally settled out, excessive water was removed to adjust the liquid volume to 22 mL. The slurry was heated to 40° C. To the slurry, 18 mL of 2M sodium hydroxide aqueous solution, 7.6 g of sodium sulfate decahydrate and 3.0 mL of glycerol polyglycidyl ether ("Denacol EX-314" manufactured by Nagase ChemteX Corporation) were added. The mixture was stirred at 40° C. for 5 hours. After the mixture was filtered, the obtained beads were washed with large amount of pure water to obtain second crosslinked beads. The slurry of the obtained second crosslinked beads and water was added into a reaction vessel. After the beads were naturally settled out, excessive water was removed to adjust the liquid volume to 29 mL.

The slurry was heated to 40° C. To the slurry, 3.7 mL of 4 M sodium hydroxide aqueous solution prepared from pure water and sodium hydroxide manufactured by Wako Pure Chemical Industries, Ltd., 7.6 g of sodium sulfate decahydrate and 2.6 g of epichlorohydrin were added. The mixture was stirred at 40° C. for 2 hours. After the mixture was filtered, the obtained beads were washed with large amount of pure water to obtain a third crosslinked beads. The obtained third crosslinked beads was added into a vessel, and pure water added thereto so that the whole volume became tenfold of the volume of cellulose beads. The mixture was heated using an autoclave at 120° C. for 60 minutes. The mixture was cooled to room temperature and then washed with distilled water of which volume was fivefold or more of the volume of the beads to obtain beads which was subjected to autoclave treatment and which was crosslinked three times. The beads is referred to as "crosslinked cellulose beads". The SEM observation image of the beads surface is shown as FIG. 2. The 20% compression stress of the beads was 0.252 MPa.

Example 1: Preparation of High-Performance Porous Cellulose Beads

The crosslinked cellulose beads prepared in Production example 1 was subjected to suction filtration for 15 minutes. In a reaction vessel, 6 g of the filtered beads were added. A buffer solution of pH 5.0 was prepared by mixing 0.1 wt % aqueous solution of citric acid monohydrate manufactured by Wako Pure Chemical Industries, Ltd. and 0.1 wt % aqueous solution of trisodium citrate manufactured by Wako Pure Chemical Industries, Ltd. To the buffer solution, cellulase (manufactured by Tokyo Chemical Industry Co., Ltd., derived from *Aspergillus niger*, Lot: YQ211-QM, specific activity: 22900 u/g) was added to be dissolved so that the concentration of cellulose became 1 wt %. In the above-described reaction vessel, 400 mL of the citrate buffer solution in which cellulase was dissolved was added. The mixture was stirred at 45° C. for 1 hour. The content in the reaction mixture was filtered and then washed with large amount of water to obtain high-performance porous cellulose beads. The SEM observation image of the obtained beads surface is shown as FIG. 3.

As shown in FIG. 2, fine pores were hardly observed on the surface of the beads which were not treated with a cellulase; on the one hand, as shown in FIG. 3, fine pores could be observed on the surface of the high-performance porous cellulose beads according to the present invention which were treated with a cellulase. In addition, the 20% compression stress of the obtained beads was 0.256 MPa. Thus, the strength was maintained regardless of the treatment with a cellulase.

Production Example 2: Production of Crosslinked Porous Cellulose Beads

Crosslinked cellulose beads were obtained by a similar method to Production example 1 except that acetonitrile in the crosslinking agent solution used in Production example 1 was replaced by isopropyl alcohol. The SEM observation image of the beads surface is shown as FIG. 4.

Example 2: Preparation of High-Performance Porous Cellulose Beads

High-performance porous cellulose beads which were treated with a cellulase were obtained by a similar method to Example 1 except that the crosslinked cellulose beads obtained Production example 2 were used. The SEM observation image of the beads surface is shown as FIG. 5.

When FIG. 4 and FIG. 5 were compared, fine pores were hardly observed on the surface of the beads which were not treated with a cellulase but fine pores could be observed on the surface of the high-performance porous cellulose beads according to the present invention which were treated with a cellulase.

Production Example 3: Production of Crosslinked Porous Cellulose Beads

Uncrosslinked porous cellulose beads were prepared similarly to Production example 1, and 20 mL of the beads was weighted and the temperature thereof was adjusted to 40° C. Then, the beads were filtered on a glass filter. The filtered beads were added into a reaction vessel. Into the reaction vessel, 12.2 mL of 2 M sodium hydroxide aqueous solution of which temperature was adjusted to 40° C. was added. The mixture was stirred for 30 minutes. Then, 24.4 mg of sodium borohydride (manufactured by Wako Pure Chemical Industries, Ltd.) and 0.5 mL of glycerol polyglycidyl ether ("Denacol EX-314" manufactured by Nagase ChemteX Corporation) were added thereto. The mixture was stirred at 40° C. for 10 minutes. Next, 7.6 g of sodium sulfate decahydrate and 6.1 mL of glycerol polyglycidyl ether ("Denacol EX-314" manufactured by Nagase ChemteX Corporation) were added thereto. The mixture was stirred at 40° C. for 4 hours and 50 minutes. After the mixture was filtered, the obtained beads were washed with large amount of pure water to obtain first crosslinked beads. Further, the obtained first crosslinked beads were subjected to the above-described crosslinking procedure from the temperature adjustment to 40° C. to the washing with large amount of water once again to obtain second crosslinked beads. The slurry of the obtained second crosslinked beads and water was added into a reaction vessel. After the beads were naturally settled out, excessive water was removed to adjust the liquid volume to 29 mL. The slurry was heated to 40° C. To the slurry, 3.7 mL of 4 M sodium hydroxide aqueous solution prepared from pure water and sodium hydroxide manufactured by Wako Pure Chemical Industries, Ltd., 7.6 g of sodium sulfate decahydrate and 2.6 g of epichlorohydrin were added. The mixture was stirred at 40° C. for 2 hours. After the mixture was filtered, the obtained beads were washed with large amount of pure water to obtain a third crosslinked beads. The obtained third crosslinked beads were added into a vessel, and pure water added thereto so that the whole volume became tenfold of the volume of the cellulose beads. The mixture was heated using an autoclave at 120° C. for 60 minutes. The mixture was cooled to room temperature and then washed with distilled water of which volume was fivefold or more of the volume of the beads to obtain beads which was subjected to autoclave treatment and which was crosslinked three times. The beads is referred to as "crosslinked cellulose beads". The SEM observation image of the torn surface of the beads is shown as FIG. 6. The 20% compression stress of the obtained beads was 0.084 MPa.

Example 3: Production of High-Performance Porous Cellulose Beads

High-performance porous cellulose beads which were treated with a cellulase were obtained by a similar method to Example 1 except that the crosslinked cellulose beads obtained Production example 3 were used. The SEM observation image of the torn surface of the beads is shown as FIG. 7.

As demonstrated by FIG. 6 and FIG. 7, the skeleton is relatively thick and the micropore volume is small within the beads which is not treated with a cellulase; one the one hand, the skeleton is relatively thin and the micropore volume is increased within the high-performance porous cellulose beads according to the present invention which is treated with a cellulase. In addition, surprisingly, though the skeleton thus becomes thinner by cellulase treatment, the strength of the obtained high-performance porous cellulose beads is improved as the 20% compression stress thereof is 0.140 MPa.

Production Example 4: Production of Adsorbent (1) Step for Producing Protein A

In accordance with Examples described in WO 2011/118699, the pentamer of modified C domains which was described in WO 2011/118699 and which had an alkali resistance was produced as modified Protein A.

(2) Step for Immobilizing Protein A

Into a centrifuge tube, 5 mL of the crosslinked porous cellulose beads obtained in Production example 3 were added. Further, RO water was added thereto so that the total volume became 7.5 mL. The centrifuge tube was set on a mixing rotor ("Mix rotor MR-3" manufactured by AS ONE Corporation) at 25° C., and the mixture was stirred. Then, 2.5 mL of 12.84 mg/mL sodium periodate aqueous solution prepared by dissolving sodium periodate in RO water was added thereto. The mixture was stirred at 25° C. for 1 hour. After the reaction, the beads were washed with RO water on a glass filter ("11GP100" manufactured by SIBATA SCIENTIFIC TECHNOLOGY LTD.) till the electrical conductivity of the filtrate became 1 µS/cm or lower to obtain formyl group-containing crosslinked porous cellulose beads. The electrical conductivity of the filtrate obtained by washing was measured using a conductivity meter ("ECTester10 Pure+" manufactured by EUTECH INSTRUMENTS).

On a glass filter ("11GP100" manufactured by SIBATA SCIENTIFIC TECHNOLOGY LTD.), 5 mL of the obtained formyl group-containing crosslinked porous cellulose beads were put. Trisodium citrate dihydrate was dissolved in RO water to obtain 0.25 M trisodium citrate aqueous solution, and the 15 mL or more of the solution was passed through the beads to replace the liquid within the beads by the trisodium citrate aqueous solution. The formyl group-containing crosslinked porous cellulose beads after the above replacement were added into a centrifuge tube using the above-described 0.25 M trisodium citrate aqueous solution. After the formyl group-containing crosslinked porous cellulose beads were settled out, the supernatant was removed to adjust the whole volume to 7.5 mL. In the slurry, 1.50 g of an aqueous solution of the above-described modified Protein A was added. The concentration of Protein A in the solution was 66.67 mg/mL. Then, the pH value of the mixture was adjusted to 12 using 0.08 N sodium hydroxide aqueous solution. The reaction was carried out at 6° C. for 23 hours with stirring by a mixing rotor ("Mix rotor MR-3" manufactured by AS ONE Corporation).

Then, 2.4M citric acid aqueous solution prepared by dissolving citric acid monohydrate in RO water was added till the pH of the reaction mixture became 5, and the mixture was subsequently stirred at 6° C. for 4 hours using a mixing rotor. Next, 1.13 mL of 5.5 wt % dimethylamine borane aqueous solution prepared by dissolving dimethylamine borane in RO water was added thereto, and the mixture was stirred at 6° C. for 1 hour. Then, the reaction temperature was increased to 25° C., and the reaction was carried out at 25° C. for 18 hours with stirring.

The beads after the reaction was washed with RO water of which volume was threefold of the volume of the beads on a glass filter ("11GP100" manufactured by SIBATA SCIENTIFIC TECHNOLOGY LTD.). Then, threefold volume amount of 0.1 M citric acid monohydrate prepared by dissolving citric acid monohydrate in RO water was added thereto. To the beads, 0.1 M citric acid monohydrate was added to adjust the whole volume to 30 mL or more. The mixture was added into a centrifuge tube and stirred at 25° C. for 30 minutes to carry out acid washing.

After the acid washing, the beads were washed with RO water of which volume was threefold of the volume of the beads on a glass filter ("11GP100" manufactured by SIBATA SCIENTIFIC TECHNOLOGY LTD.). Next, threefold amount of 0.05 M sodium hydroxide prepared by dissolving sodium hydroxide in RO water and 1 M sodium sulfate aqueous solution prepared by dissolving sodium sulfate in RO water were respectively added. Then, 0.05 M sodium hydroxide and 1 M sodium sulfate aqueous solution were added to adjust the whole amount to 30 mL or more. The mixture was added into a centrifuge tube and stirred at room temperature for 30 minutes to carry out alkaline washing.

After the alkaline washing, the beads was washed with RO water of which volume was 20-fold of the volume of the beads on a glass filter ("11GP100" manufactured by SIBATA SCIENTIFIC TECHNOLOGY LTD.). Next, threefold amount of 0.1 M sodium citrate aqueous solution prepared by dissolving trisodium citrate dihydrate in RO water was added. After it was confirmed that the filtrate became neutral, washing was carried out with RO water till the electrical conductivity of the filtrate became 1 µS/cm or lower to obtain an adsorbent on which Protein A was immobilized. The electrical conductivity of the filtrate obtained by washing was measured using a conductivity meter ("ECTester10 Pure+" manufactured by EUTECH INSTRUMENTS). The 5% DBC of the adsorbent at RT of 3 min was 22.0 g/L.

Example 4: Preparation of Adsorbent

An adsorbent was obtained similarly to Production example 4 except that the high-performance porous cellulose beads obtained by Example 3 were used. The 5% DBC of the adsorbent at RT of 3 min was 24.4 g/L. As such a result, the adsorption performance of the adsorbent containing the high-performance porous cellulose beads treated with a cellulase was improved in comparison with an ordinary adsorbent.

The invention claimed is:

1. An adsorbent, comprising porous cellulose beads produced by a method comprising treating crosslinked cellulose beads with a cellulolytic enzyme and a ligand interacting with a target substance to be adsorbed.

2. The adsorbent according to claim 1, wherein an endo cellulolytic enzyme is used as the cellulolytic enzyme.

3. The adsorbent according to claim 2, wherein an exo cellulolytic enzyme is further used as the cellulolytic enzyme.

4. The adsorbent according to claim 1, wherein the crosslinked cellulose beads are treated with the cellulolytic enzyme for from 1 hour to 10 hours.

5. The adsorbent according to claim 1, wherein the crosslinked cellulose beads are crosslinked by a glycidyl ether compound as a crosslinking agent.

6. The adsorbent according to claim 1, wherein the crosslinked cellulose beads are crosslinked using water as a reaction solvent for a crosslinking reaction.

7. A purification method, comprising contacting the adsorbent according to claim 1 with a solution comprising the target substance to be adsorbed.

* * * * *